United States Patent
Lott

(10) Patent No.: US 9,402,927 B2
(45) Date of Patent: Aug. 2, 2016

(54) DEVICE FOR STERILIZATION BY ULTRAVIOLET RADIATION

(71) Applicant: Heraeus Noblelight GmbH, Hanau (DE)

(72) Inventor: Josef Zoltan Lott, Hamburg (DE)

(73) Assignee: Heraeus Noblelight GmbH, Hanau (DE)

( * ) Notice: Subject to any disclaimer, the term of this patent is extended or adjusted under 35 U.S.C. 154(b) by 0 days.

(21) Appl. No.: 14/675,951

(22) Filed: Apr. 1, 2015

(65) Prior Publication Data
US 2015/0283279 A1    Oct. 8, 2015

(30) Foreign Application Priority Data

Apr. 4, 2014 (DE) .......................... 10 2014 104 851

(51) Int. Cl.
*A61L 2/10* (2006.01)
*G01F 1/76* (2006.01)
*A61L 9/20* (2006.01)

(52) U.S. Cl.
CPC ... *A61L 2/10* (2013.01); *A61L 9/20* (2013.01); *G01F 1/76* (2013.01)

(58) Field of Classification Search
USPC ........ 250/453.11, 454.11, 455.11; 422/22, 24
See application file for complete search history.

(56) References Cited

U.S. PATENT DOCUMENTS

| 6,646,278 | B1 | 11/2003 | Schwarz et al. | |
|---|---|---|---|---|
| 8,382,008 | B1* | 2/2013 | Ricciardi | A61L 2/22 128/200.16 |
| 2004/0108472 | A1* | 6/2004 | Maruo | G01N 21/552 250/504 R |
| 2004/0219057 | A1* | 11/2004 | Golden | A61L 2/088 422/24 |
| 2014/0231671 | A1* | 8/2014 | Lu | B05D 3/067 250/455.11 |

FOREIGN PATENT DOCUMENTS

DE          19527472 C1    3/1997
DE   10 2005 026 645 A1   2/2007

OTHER PUBLICATIONS

Office Action issued Dec. 1, 2015 in Application No. DE 102014104851.2.

* cited by examiner

*Primary Examiner* — Nicole Ippolito
(74) *Attorney, Agent, or Firm* — Panitch Schwarze Belisario & Nadel LLP

(57) ABSTRACT

In a known device for sterilization by ultraviolet radiation, a UV radiator (4) is arranged in a housing (2) made of metal or plastic, which has a radiation outlet window (3) for the emission of UV radiation. The radiation outlet window is covered by a polymer film (7) transparent to ultraviolet radiation. Proceeding from this background, in order to provide a reliable and operationally safe device for sterilization, it is proposed that the housing (2) have a gas inlet (22) for introduction of a cooling gas stream as well as a gas outlet (23) for discharging the cooling gas stream, and that the gas outlet (23) be connected to a measuring sensor (17; 18, 20, 21) for measuring the pressure, mass flow rate, and/or volumetric flow rate of the discharged cooling gas stream.

13 Claims, 2 Drawing Sheets

DEVICE FOR STERILIZATION BY ULTRAVIOLET RADIATION

BACKGROUND OF THE INVENTION

1. Field of the Invention

The present invention relates to a device for sterilization by ultraviolet radiation, comprising a UV radiator arranged in a housing made of metal or plastic, which has a radiation outlet window for emitting UV radiation covered by a polymer film that is transparent for ultraviolet radiation.

2. Prior Art

UV radiators are used for sterilization, for example in air-conditioning and drinking water systems, as well as in food production. Here, both food, such as fruit and vegetables, and also machine parts, packaging materials, liquids, air and surfaces that come in contact with the food during its preparation are irradiated. The UV radiators are typically surrounded by a quartz glass jacket tube and can be arranged in the direct vicinity of or at a greater distance from the goods to be irradiated, for example as an overhead fitting for air and surface sterilization. One disadvantage is that, if the quartz glass jacket tube breaks, fragments can get into or onto the goods to be irradiated. To prevent this, a plurality of safety devices are known that require, however, a certain amount of expense in terms of measures and materials.

This disadvantage is avoided by a sterilization device of the type mentioned at the outset, as known, for example, from German published patent application DE 10 2005 026 645 A1. Therein it is proposed to hold the UV radiator surrounded by a quartz glass jacket tube in a cylindrical metal or plastic housing equipped with a radiation outlet window for emitting UV radiation. A film made of a fluoropolymer (MFA) is shrunk-fit over the housing and the radiation outlet window. This film has a high degree of transparency for radiation with wavelengths around 253.7 nm.

TECHNICAL OBJECT

In normal use the UV radiators and the housings surrounding them, as well as the UV-transparent plastic films, are exposed to high temperatures, water, water vapor, or even corrosive and caustic substances and are thereby subject to high thermal, mechanical, and chemical loads.

These conditions can lead to aging and damage of the plastic film, so that foreign particles, dust, or liquids can penetrate into the housing and negatively affect the optical and electrical components located there and, in particular, the output of the UV lamp.

BRIEF SUMMARY OF THE INVENTION

The invention is therefore based on the object of avoiding this disadvantage and providing a reliable and operationally safe device for sterilization.

This object is achieved according to the invention starting from a device of the type mentioned at the outset, in that the housing has a gas inlet for introducing a cooling gas stream as well as a gas outlet for discharging the cooling gas stream, and in that the gas outlet is connected to a measuring sensor for measuring pressure, mass flow rate, and/or volumetric flow rate of the discharged cooling gas stream.

The housing protecting the UV radiator from contamination, temperature, and liquids is provided with an inlet and with an outlet for the cooling gas. With the cooling gas the UV radiator can be maintained at a predetermined temperature, which also enables the use of high-power radiators that require cooling. Therefore, a jacket tube additionally surrounding the UV radiator—as with the above-mentioned prior art—can therefore be eliminated with the invention.

With the invention, the cooling gas stream fulfills another essential function. It serves as a test gas flow for detecting leaks in the housing, particularly the leak-tightness of the polymer film. For this purpose, a measuring sensor is provided that enables at least the measurement of pressure, mass flow rate, and/or volumetric flow rate of the discharged cooling gas stream. If there are unexpected fluctuations in one or more of these parameters or if there is a deviation from a specified desired value, a leak can be assumed. The gas outlet is connected to the measuring sensor directly or indirectly—via one or more other components.

The housing preferably comprises metal, particularly stainless steel. It surrounds one or more UV radiators and/or other radiators. UV radiators in this sense are, for example, low-pressure mercury vapor radiators, medium-pressure mercury vapor radiators, or high-pressure mercury vapor radiators. Preferably, the lines for the electrical connection of the UV radiator also run inside the housing, and they are transferred to the housing via supply or discharge pipes for the cooling gas stream. In this way, separate housing openings for the operating lines and data lines are avoided, which contributes to leak-tightness.

It has proven favorable if the measuring sensor comprises a first sensor connected to the gas inlet and a second sensor connected to the gas outlet.

By the first upstream sensor, viewed in the direction of flow, the parameter to be measured—that is, volumetric flow rate, mass flow rate, or gas pressure—of the introduced cooling gas stream is determined continuously. The relevant parameter is also measured for the discharged cooling gas stream by the second, downstream sensor continuously or from time to time. If there is a noticeable discrepancy between the two measured values, for example a pressure drop deviating from a specified limit value or a significant difference between the mass flow rate or volumetric flow rate on the two sides of the housing, a leak can be assumed. The measured values determined by the sensors, particularly the measured value determined by the upstream sensor, can simultaneously be used for controlling the cooling gas stream for the purpose of controlling the temperature of the UV radiators.

In the simplest case, at least the first sensor, preferably also the second sensor, is constructed as a mass flow rate regulator.

Mass flow rate regulators are reliable and precise and suitable not only for regulating the gas mass flow rate, but also for simple measurements.

Here, it has proven favorable if the measuring sensor comprises an indicator or alarm device.

In this way, it is ensured that a leak does not remain undetected over a long period of time, but instead remedial measures can be introduced immediately after the occurrence of an irregularity. These measures can also include an automatic shutdown of the device, particularly if the measuring sensor comprises an evaluation and disconnecting device adapted for this purpose.

In a preferred embodiment of the device according to the invention, the UV radiator is part of a lamp unit arranged inside the housing and has two UV radiators and one IR radiator.

The infrared radiator is used for shortening the warm-up period of the UV radiators during startup and for faster operational readiness of the device. It is preferably arranged centrally between the two UV radiators.

Together with the plastic or metal housing, the lamp unit made up of UV radiators and an infrared radiator forms an operationally ready, preassembled radiator module. For use in the sterilization device, only the polymer film still must be applied for covering the radiation inlet window, and the electrical connections and the gas connections for discharging and feeding the cooling gas must be made.

In this context, it has proven advantageous if the UV radiators are provided with a reflector on their side facing away from the radiation outlet window.

The reflector preferably involves a coating of the lamp bulb of the UV lamps with reflective properties, for example a coating made of opaque quartz glass.

In the area of the radiation outlet window, the housing advantageously has an elongated oval or rectangular cross section.

At least one of the housing sides is here essentially flat. If the radiation outlet window runs completely in the area of this flat side, then the longitudinal edges of the radiation outlet window lie exactly opposite in a common plane. In this way, a defined tension plane is created for the polymer film, which counteracts folding and warping of the film.

It has proven effective when the measuring sensor comprises a temperature sensor for detecting the temperature of the UV radiator.

The effectiveness of the UV radiation emission depends significantly on the operating temperature. The temperature sensor continues to detect the temperature of the UV radiator, that is, continuously or from time to time. For the simultaneous use of several UV radiators, each of the radiators can be provided with a temperature sensor. Alternatively, only the temperature on one radiator or individual radiators could also be detected. The temperature is preferably detected on the surface of the radiator tube. Through the continuing detection of the radiator temperature it is possible to detect deviations of the radiator temperature from a specified desired value and to compensate for these deviations, for example by changing the cooling gas stream.

In this context it is also advantageous if the gas inlet is connected to a temperature control device by which the temperature of the cooling gas stream can be controlled.

Deviations of the radiator temperature from the nominal operating temperature can involve, for example, a high ambient temperature or could be dependent on the construction of the irradiation device. A temperature-controllable cooling gas stream could also be heated, so that the temperature of the UV radiator could be kept in the desired temperature range more quickly and more precisely. A temperature control device arranged in a feed channel for the cooling gas stream has the advantage that the temperature of the cooling gas is controlled in spatial proximity to the UV radiator.

The device can be provided with a plurality of lines, for example with supply lines for media, such as liquids or gases, with measurement and data lines from and to sensors, actuators, or computers, or with power supply lines.

To prevent obstructions by these lines or damage to the lines, it has proven effective if a cooling gas guide tube is connected to the gas inlet and/or—preferably—to the gas outlet, with supply or data lines being led through this guide tube.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. Shown in detail in schematic representations are.

DETAILED DESCRIPTION OF THE INVENTION

Figure 1:
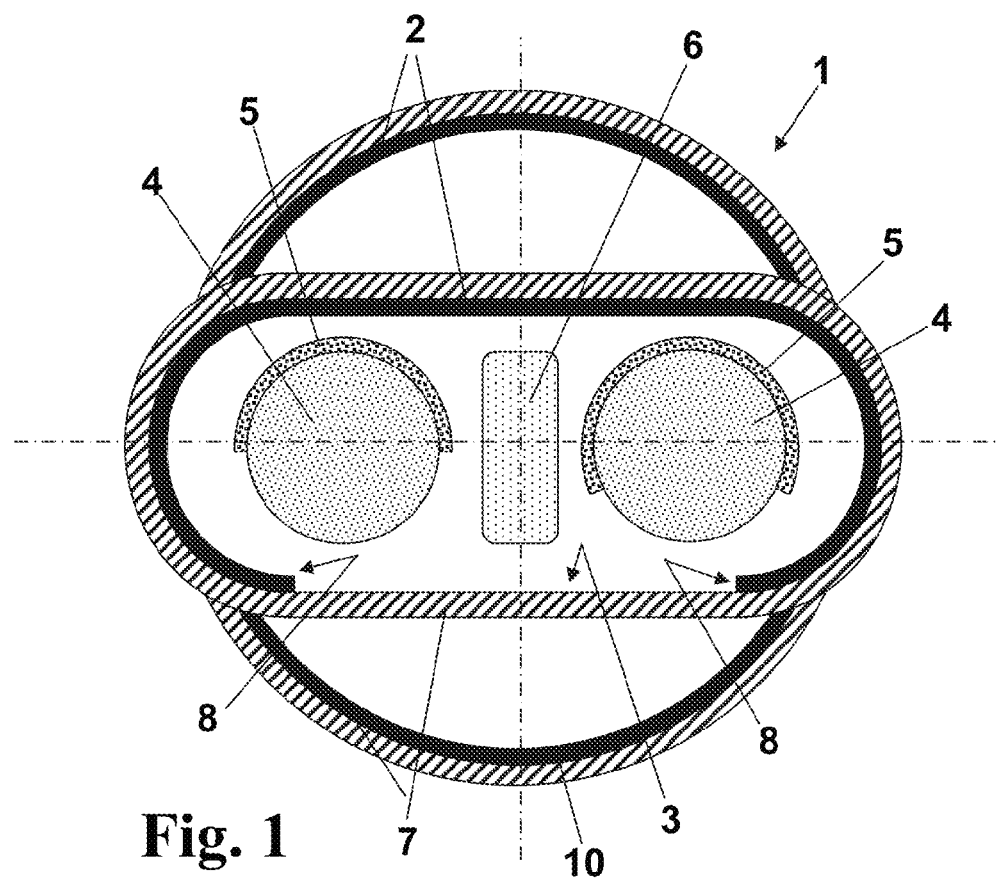
FIG. 1 is a cross-sectional view of a radiator module for use in a sterilization device according to an embodiment of the invention having a metal tube, two UV lamps, and an infrared radiator, in the region of the longitudinal center of the metal tube.

FIG. 1 shows schematically a radiator module 1 for use in the device according to an embodiment of the invention for sterilization of packaging material for food.

In the embodiment the radiator module 1 comprises an approximately 1.5 mm thick metal tube 2 made of stainless steel, whose end regions 10 on both sides have circular cross sections having an outer diameter of 70 mm and whose center part is flattened and has an elongated oval cross section, as can be seen in the cross section of FIG. 1. The metal tube 2 including the flattened middle part forms a housing inner space defined by two flat sides connected to each other by rounded side walls. A radiation outlet window 3 is cut into one of the flat sides.

In the metal tube housing there are two UV radiators 4 running parallel to each other with their longitudinal axes. The side of the UV radiators 4 facing away from the radiation outlet window 3 is provided with a reflector coating 5 made of opaque, diffusely reflective quartz glass. In the center between the two UV radiators 4 there is an infrared radiator 6. The length of the radiation outlet window 3 corresponds to the illuminated length of the UV radiators 4.

The UV radiators 4 are low-pressure amalgam radiators having an illuminated tube made of quartz glass, which encloses a discharge space and is closed at both ends with pinched sections through which the power supply is guided. Within and at opposite ends of the illuminated tube there are two coil-shaped electrodes. The discharge space is filled with a gas mixture made of argon and neon (50:50). Inside the discharge space there is also an amalgam charge. The low-pressure amalgam radiator 4 is operated with an essentially constant lamp current. The nominal power output is 200 W (at a nominal lamp current of 4.0 A), the illuminated length is 50 cm, the radiator outer diameter is 28 mm, and it is distinguished by a power density of approximately 4 W/cm.

The infrared radiator 6 is used as an external energy source for heating the two UV radiators 4. It is constructed as a so-called twin-tube radiator, in which the bulb has two sub-spaces that are parallel to each other and which are separated from each other by a center connecting piece. Within each of the sub-spaces there is a heating coil made of tungsten in an argon protective gas. The nominal power output of the IR radiator 6 (at a nominal lamp current of 8 A) is 2,000 W. The outer dimensions of the twin-tube radiator 6 are 23×11 mm and the illuminated lamp length corresponds approximately to that of the UV radiator 4. It is distinguished by a power density of approximately 125 W/cm.

The module composed of metal housing 2, UV radiators 4, and IR radiator 6 is surrounded by a 0.5 mm thick UV-transparent polymer hose 7 (fluoropolymer MFA-perfluoro methyl alkoxy), which seals the radiation outlet window 3. The polymer hose 7 is here drawn over the entire length of the metal tube 2 up to the ends. In this way, the flattening in the middle part of the metal tube 2 has the effect that the longitudinal edges 8 in the region of the ground-in radiation outlet window 3 lie exactly opposite in a common plane. In this way, a defined tension place is created for the polymer hose 7, which prevents folding and warping in the region of the radiation outlet window 3.

Figure 2:
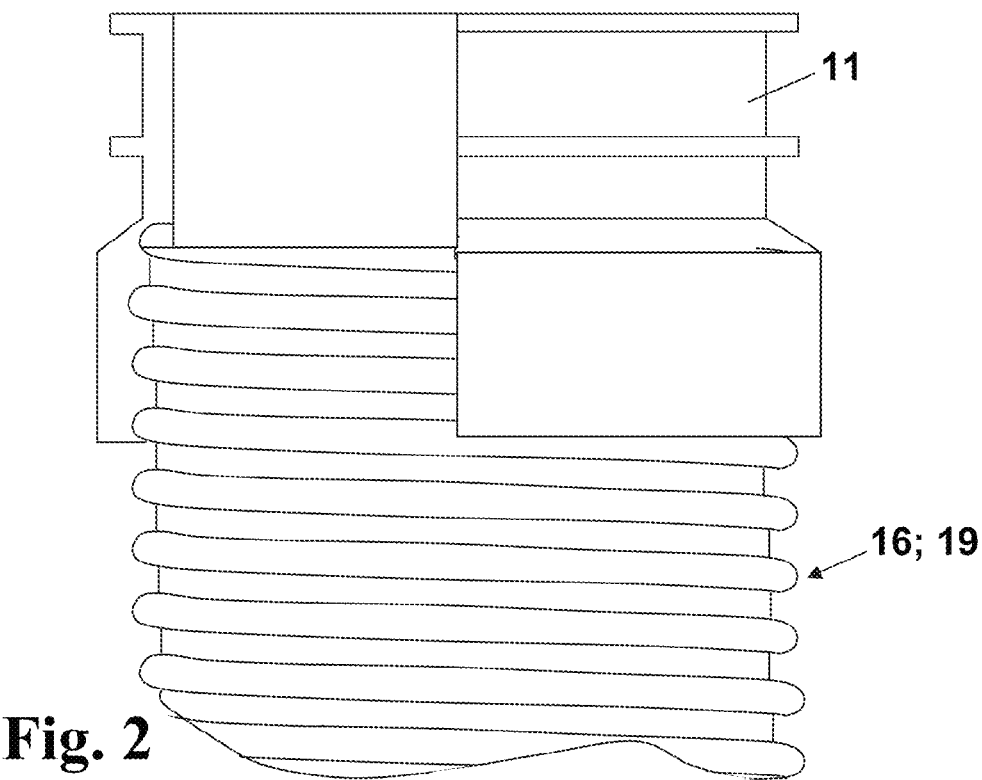
FIG. 2 is a cutout of an embodiment of a cooling gas guide tube for water-tight connection to the radiator module according to FIG. 1.
Figure 3:
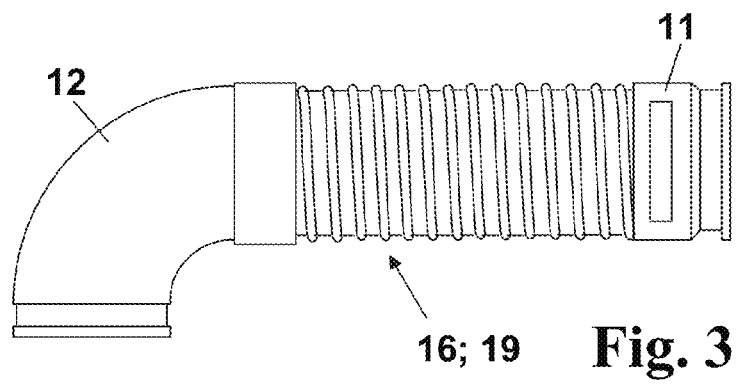
FIG. 3 is a reduced, complete lateral representation of the cooling gas guide tube (hose) according to FIG. 2.

The ends of the metal housing 2, that cannot be seen in FIG. 1, are open and have a circular cross section. The open housing ends 10 serve for the feeding and discharging of a cooling gas stream for air cooling of the module 1. For this purpose, the ends 10 are connected to cooling gas spiral hoses 16; 19 made of polyurethane, as shown in FIGS. 2 and 3. On one end, a sleeve 12 fitting the housing 2 of the module 1 is cast onto each cooling gas hose (see FIG. 3), which sleeve serves for a water-tight connection to the housing. The other end is provided with a connecting part 11 for other connecting elements, for example extension tubes or measuring sensors. The sleeves 12 have a straight projection or they are angled as shown in FIG. 3.

The cooling gas hoses serve for feed 16 or discharge 19 of a cooling gas stream, particularly an air flow, to and from the radiator module 1 and at the same time, the electrical supply cables for the radiator module 1 and data lines also run in these hoses. Thus, the radiator module 1 does not require additional openings for the connection of electrical supply lines.

The cooling gas flushing serves to cool/control the temperature of the UV radiator 4 and its reflectors 5. In the embodiment, air is used as the cooling gas. If, instead, an inert gas is used, such as nitrogen, this allows a non-ignitable atmosphere to be maintained in the housing inner space, which contributes to explosion protection. In addition, the cooling also prolongs the service life of the polymer hose 7. Thus, for a UV irradiation time of more than 10,000 hours, no significant changes are ascertained to the optical transmission or to the mechanical stability of the polymer hose 7.

Figure 4:
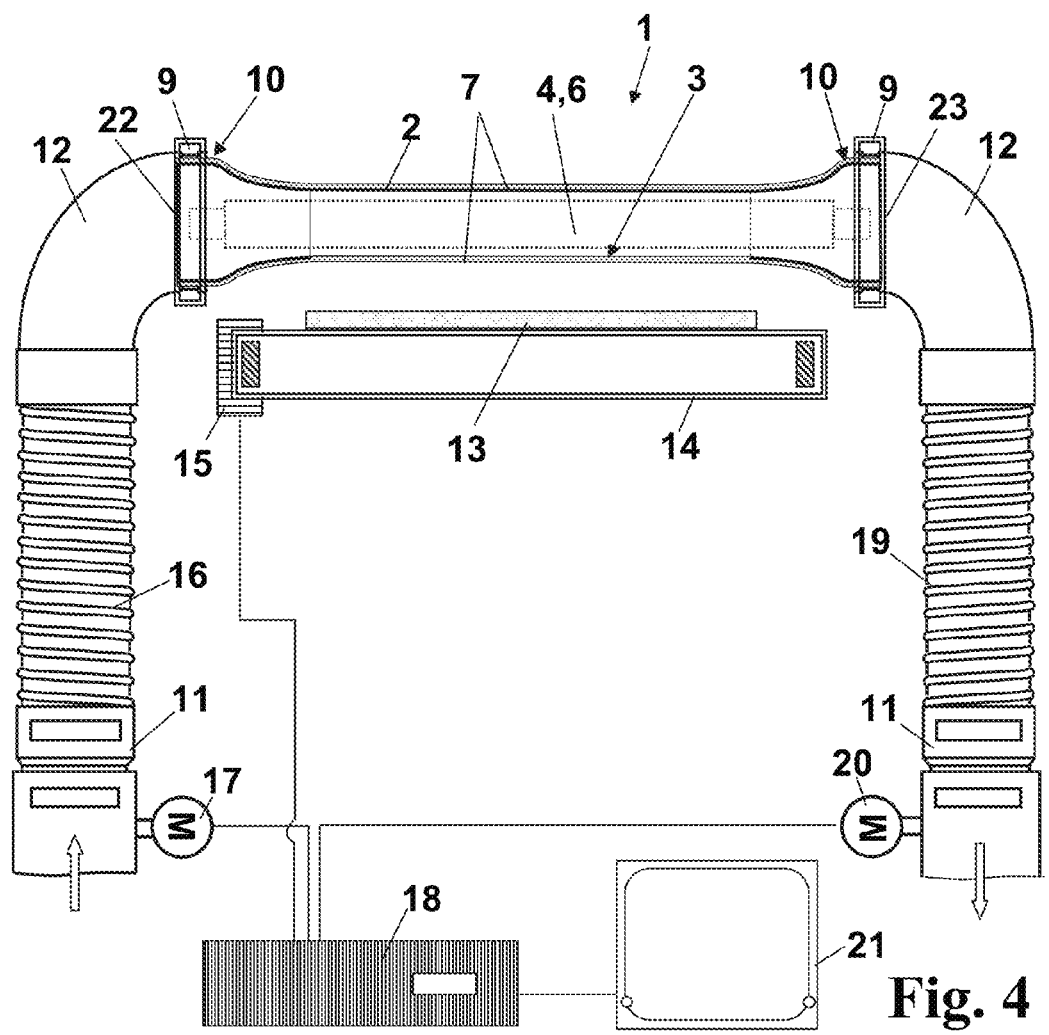
FIG. 4 is an overall schematic view of an embodiment of the device for sterilization according to the invention having the radiator module of FIG. 1 and the cooling gas guide tube of FIGS. 2 and 3.

Another essential function of the cooling gas stream in the sense of the invention will be explained in more detail below with reference to the schematic representation of the overall device in FIG. 4 for sterilization.

In addition to the radiator module 1 already explained above, the irradiation device 1 comprises a conveyor belt 14 moved by a drive motor 15, on which belt the food packaging material 13 to be irradiated lies and is continuously fed to the radiator module 1.

The tubular metal housing 2 of the radiator module 1 is closed at the ends with the cooling gas hoses 16; 19. The two UV radiators 4 and the IR radiator 6 are indicated with dotted-line outlines. They lie one behind the other in the view of FIG. 4 in the plane of the paper and are each inserted with their sockets into holding elements that are mounted on the end 10 of the tube. The gas inlet of the housing 2 is marked with the reference numeral 22 and the gas outlet is marked with the reference numeral 23. The cast-on hose sleeve 12 here encompasses the round tube end 10 of the metal housing 2 together with the drawn-on polymer hose 7 and is pressed against the outer circumference of the tube end by a hose clamp 9.

The cooling gas hose 16 for feeding the cooling air stream is equipped with a mass flow rate regulator 17. This is connected to an evaluation and control unit 18. The mass flow rate of the cooling air stream is typically in the range of 50 to 100 m³/hr.

The cooling gas hose 19 for discharging the cooling air stream also serves for feeding all electrical cables for operating the radiator module 1 and also for a signal line to a temperature sensor arranged inside the radiator module housing 2 and which detects the surface temperature of one of the UV radiators. The cooling gas hose 19 is equipped with a mass flow rate measuring element 20 for the discharged cooling air and is also connected to the evaluation and control unit 18.

The evaluation and control unit 18 is connected to the said temperature sensor, which detects the surface temperature of one of the UV radiators 4, and also to another temperature sensor (not shown in the Fig.) for measuring the surface temperature of the packaging material 13 to be irradiated.

The evaluation and control unit 18 serves for temperature control, by which the surface temperature of the UV radiator 5 is the controlled parameter. The actuating parameter here is the cooling gas stream, which is set by the evaluation and control unit 18 via the mass flow rate regulator 17.

Simultaneously and continuously, the evaluation and control unit 18 monitors the mass flow rate of the discharged cooling air stream via the measuring element 20. The measured data are simultaneously displayed on a monitor 21. If a deviation between an introduced and discharged air flow is detected, which is greater than a specified limit value by 10% of the introduced air flow, then the evaluation and control unit 18 immediately switches off the drive 15 for the conveyor belt 14 and the radiator module 1 and outputs an acoustic alarm as well as a corresponding indication on the monitor 21. For especially strict requirements on leak tightness of the radiator module 1, as an alternative to or in addition to the measurement of the mass flow rate of the cooling air stream, a gas pressure measurement is provided, by which the gas pressure of the discharged cooling air stream is continuously monitored and evaluated.

Through the use of the polymer film 7 for the sealed closure of the radiation outlet window 3, the sterilization device according to the invention is water-tight. Even though an expensive quartz glass jacket tube is eliminated for the radiator module 1, the device is more operationally safe despite the more economical construction, because the leak tightness of the seal is continuously monitored.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device for sterilization by ultraviolet radiation, the device comprising a UV radiator arranged in a housing made of metal or plastic, the housing having a radiation outlet window for emission of UV radiation, the window being covered by a polymer film transparent to ultraviolet radiation, wherein the housing has a gas inlet for introducing a cooling gas stream and a gas outlet for discharging the cooling gas stream, and wherein the gas outlet is connected to a measuring sensor for measuring at least one of pressure, mass flow rate, and volumetric flow rate of the discharged cooling gas stream.

2. The device according to claim 1, wherein the measuring sensor comprises a first sensor connected to the gas inlet and a second sensor connected to the gas outlet.

3. The device according to claim 2, wherein at least the first sensor comprises a mass flow rate regulator.

4. The device according to claim 2, wherein the measuring sensor further comprises an indicator or alarm.

5. The device according to claim 1, wherein the measuring sensor further comprises an indicator or alarm.

6. The device according to claim 1, wherein the measuring sensor further comprises an evaluation and control device.

7. The device according to claim 1, wherein the UV radiator is part of a lamp unit arranged inside the housing, the lamp unit comprising two UV radiators and an IR radiator.

8. The device according to claim 7, wherein at least the two UV radiators have a reflector on their side facing away from the radiation outlet window.

9. The device according to claim 8, wherein the housing has an elongated oval or rectangular cross section in a region of the radiation outlet window.

10. The device according to claim 7, wherein the housing has an elongated oval or rectangular cross section in a region of the radiation outlet window.

11. The device according to claim 1, wherein the measuring sensor comprises a temperature sensor for detecting temperature of the UV radiator.

12. The device according to claim 1, wherein the gas inlet is connected to a temperature control by which temperature of the cooling gas stream is controlled.

13. The device according to claim 1, further comprising a cooling gas guide tube attached to at least one of the gas inlet and the gas outlet and through which at least one of power supply and data lines is guided.

* * * * *